United States Patent
Ba et al.

(10) Patent No.: US 10,458,969 B2
(45) Date of Patent: Oct. 29, 2019

(54) DYNAMIC WATER QUALITY PREDICTION

(71) Applicant: INTERNATIONAL BUSINESS MACHINES CORPORATION, Armonk, NY (US)

(72) Inventors: Amadou Ba, Dublin (IE); Radu Marinescu, Dublin (IE); Sean A. McKenna, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 203 days.

(21) Appl. No.: 15/077,363

(22) Filed: Mar. 22, 2016

(65) Prior Publication Data

US 2017/0276660 A1    Sep. 28, 2017

(51) Int. Cl.
  *G01N 33/18* (2006.01)
  *G06Q 10/04* (2012.01)
  *G06Q 50/06* (2012.01)

(52) U.S. Cl.
  CPC ......... *G01N 33/1826* (2013.01); *G06Q 10/04* (2013.01); *G06Q 50/06* (2013.01)

(58) Field of Classification Search
  CPC .................................................. G01N 33/1826
  See application file for complete search history.

(56) References Cited

U.S. PATENT DOCUMENTS 5,581,459 A * 12/1996 Enbutsu ............... G05B 13/027
                                                        364/152
7,391,333 B2   6/2008 Madden et al.
(Continued)

FOREIGN PATENT DOCUMENTS

CA      2634759 A1   12/2009
EP      0493819 B1    8/1995
(Continued)

OTHER PUBLICATIONS

Weihui Deng et al., "A novel hybrid water quality time series prediction method based on cloud model and fuzzy forecasting", Chemometrics and Intelligent Laboratory Systems 149, 2015, pp. 39-49.

*Primary Examiner* — Christine A Enad
(74) *Attorney, Agent, or Firm* — Cantor Colburn LLP; Kurt Goudy (57) ABSTRACT

Technical solutions are described for predicting water quality of a water source over a forecast horizon and for multiple locations. An example computer-implemented method includes receiving a forecast horizon for across which to predict the water quality. The forecast horizon includes a plurality of time periods. The computer-implemented method also includes receiving one or more geographical locations at which to predict the water quality. The computer-implemented method also includes receiving a set of water quality measures for the water source. The computer-implemented method also includes determining predicted water quality measures for the geographical location at each of the plurality of time periods in the forecast horizon based on the water quality measures. The computer-implemented method also includes outputting one or more of the predicted water quality measures.

17 Claims, 6 Drawing Sheets

(56) References Cited

U.S. PATENT DOCUMENTS

| | | | | |
|---|---|---|---|---|
| 7,920,983 | B1* | 4/2011 | Peleg | G01M 3/2807 |
| | | | | 702/100 |
| 8,886,482 | B2* | 11/2014 | Higgins | G05B 15/02 |
| | | | | 340/870.16 |
| 2005/0207939 | A1 | 9/2005 | Roussi et al. | |
| 2007/0233397 | A1* | 10/2007 | Kim | G01N 33/1846 |
| | | | | 702/19 |
| 2007/0257806 | A1* | 11/2007 | Madden | G01N 33/18 |
| | | | | 340/603 |
| 2011/0307203 | A1 | 12/2011 | Higgins et al. | |
| 2014/0012556 | A1* | 1/2014 | Lee | G06F 17/5009 |
| | | | | 703/9 |
| 2014/0107939 | A1* | 4/2014 | Jaunakais | G01N 33/18 |
| | | | | 702/22 |
| 2015/0323514 | A1* | 11/2015 | Chen | G01N 33/18 |
| | | | | 702/25 |
| 2016/0340206 | A1* | 11/2016 | Antos | C02F 1/008 |
| 2017/0083747 | A1* | 3/2017 | Guan | G06K 9/0063 |
| 2017/0270446 | A1* | 9/2017 | Starr | G06Q 10/06313 |
| 2017/0277815 | A1* | 9/2017 | Lorang | G06F 17/5009 |

FOREIGN PATENT DOCUMENTS

| | | | |
|---|---|---|---|
| EP | 1794583 | A1 | 6/2007 |
| WO | 2006036929 | A1 | 4/2006 |
| WO | 2013136503 | A1 | 9/2013 |
| WO | 2014157753 | A1 | 10/2014 |
| WO | 2015147349 | A1 | 10/2015 |

\* cited by examiner

DYNAMIC WATER QUALITY PREDICTION

BACKGROUND

The present application relates to water supply systems, and more specifically, to predicting quality of water in water sources used by the water supply systems.

Monitoring water sources for quality, or contamination, ensures safety of the society. For example, consumers of water from the water sources may be warned in response to detecting a contamination of the water. Predicting water quality further facilitates such safety by enabling preventative steps to be taken. Thus, predicting water quality can avoid cost of potentially expensive reactive measures to resolve the contamination. Potential sources for contamination of water sources include naturally occurring phenomena as well as human-induced events. The pervasiveness of such threats beckons for an accurate and reliable apparatus and method for detecting and predicting whether water sources are and will be contaminated.

SUMMARY

According to an embodiment, a computer-implemented method for predicting water quality of a water source includes receiving a forecast horizon for across which to predict the water quality. The forecast horizon includes a plurality of time periods. The computer-implemented method also includes receiving one or more geographical locations at which to predict the water quality. The computer-implemented method also includes receiving a set of water quality measures for the water source. The computer-implemented method also includes determining predicted water quality measures for the geographical location at each of the plurality of time periods in the forecast horizon based on the water quality measures. The computer-implemented method also includes outputting one or more of the predicted water quality measures.

According to another embodiment, a system for predicting water quality of a water source includes a memory; and a processor. The processor receives a forecast horizon for across which to predict the water quality, where the forecast horizon includes a plurality of time periods. The processor further receives a one or more geographical locations at which to predict the water quality. The processor further receives a set of water quality measures for the water source. The processor determines predicted water quality measures for the geographical location at each of the plurality of time periods in the forecast horizon based on the water quality measures. The processor outputs one or more of the predicted water quality measures.

According to another embodiment, a computer program product for predicting water quality of a water source includes a computer readable storage medium. The computer readable storage medium includes computer executable instructions to receive a forecast horizon for across which to predict the water quality. The forecast horizon includes a plurality of time periods. The computer readable storage medium includes computer executable instructions to receive one or more—geographical locations at which to predict the water quality. The computer readable storage medium includes computer executable instructions to receive a set of water quality measures for the water source. The computer readable storage medium includes computer executable instructions to determine predicted water quality measures for the geographical location at each of the plurality of time periods in the forecast horizon based on the water quality measures. The computer readable storage medium includes computer executable instructions to output one or more of the predicted water quality measures.

BRIEF DESCRIPTION OF THE DRAWINGS

The examples described throughout the present document may be better understood with reference to the following drawings and description. The components in the figures are not necessarily to scale. Moreover, in the figures, like-referenced numerals designate corresponding parts throughout the different views.

DETAILED DESCRIPTION

Disclosed here are technical solutions for monitoring and predicting water quality of a water source, such as a river basin. The technical solutions facilitate predicting the water quality across a time horizon, which includes a number of time-periods, such as weeks, months, or the like. Additionally, the technical solutions facilitate predicting the water quality across a set of locations, such as along the river. The technical solutions predict the water quality using dynamic probabilistic graphical models, such as based on Bayesian network. The technical solutions further facilitate identifying hazardous events based on the predicted water quality. For example, a system implementing the technical solutions herein predicts water quality of water periodically, such as daily/weekly/monthly, and alerts a user when safety thresholds are exceeded. The user may be a local governing body, a water management organization, or consumers that use the water from the water source. The technical solutions further facilitate providing additional information about the predicted water quality, for example an explanation of the predicted hazardous event, thus enabling a user to take precautionary and/or remedial measures in response.

Figure 1A:
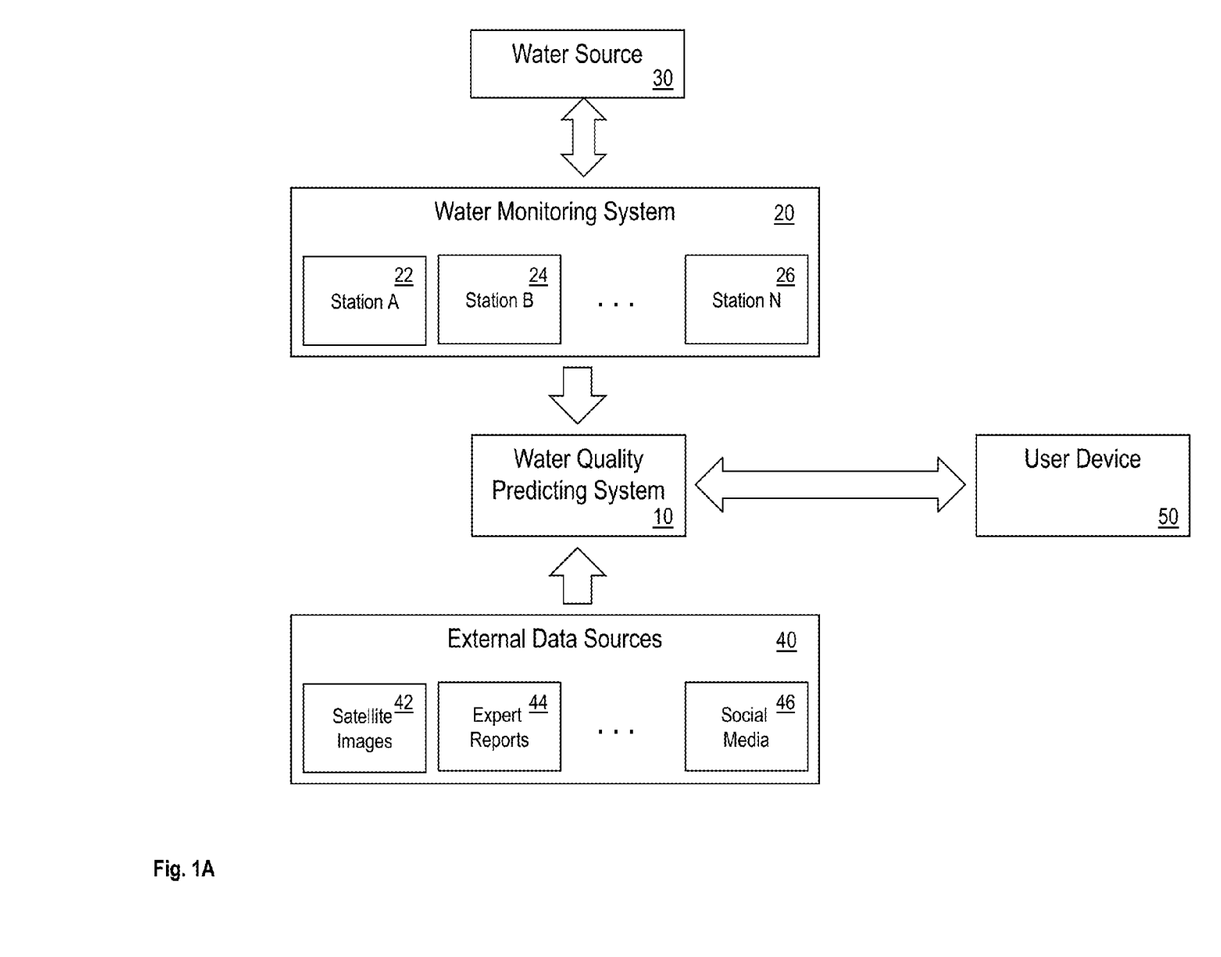
FIG. 1A illustrates an example water quality predicting system in accordance with an embodiment.

FIG. 1 illustrates an example water quality predicting system 10 that uses water quality measurements from a water source monitoring system 20. The water monitoring system 20 monitors a water source 30. The water quality predicting system 10 may further use data from external data source 40 to provide information to a user device 50.

The water source 30 may be a source of water supply, such as a river basin, a lake, a stream, or any other water source. The water source 30 may also be a man-made water supply, such as a well, a water distribution network or any other such water source. In addition, the water source 30 may be a combination of a natural water supply and a man-made water source, such as any combination of the above listed examples.

The water monitoring system 20 may be system that measures water quality parameters of the water in the water source 30. For example, the water monitoring system 20 may include one or more water monitoring stations, such as a station-A 22, a station-B 24, and so on until a station-N 26. The monitoring stations may be located along the flow of the water source. For example, the station-A 22 may be upstream from the station-B 24 and the station-N 26. Similarly, in the illustrated example, the station-B 24 may be upstream from the station-N 26. The monitoring stations may be located at predetermined locations on the water source 30, such as at a pumping station, a junctions in a water distribution network, a filtering station, an intake/catching station, or any other such predetermined location along the water source 30. The monitoring stations may collect water quality measurements of the water at their respective geographical locations. For example, the water quality measurements may include measures of water pressure, flow-rate, temperature, turbidity, chlorine content, dissolved oxygen content, chlorophyll content, dissolved nutrient content, and other such water quality measures. The monitoring stations and/or the water monitoring system 20 may maintain records of the water quality measurements for a predetermined duration, such as for the past five years, past two years, past two weeks, or any other duration. The monitoring stations may record the water quality measures according to a predetermined schedule, such as every hour, every day, every week, and so on. The monitoring stations may further facilitate measuring the water quality measures on demand.

In addition, the water monitoring system 20 facilitates providing the recorded water quality measures from each of the monitoring stations upon request. For example, the water quality predicting system 10 may request the water monitoring system 20 for water quality measures at a specific monitoring station, such as the station-A. In response, the water quality predicting system 10 receives the requested water quality measure sent by the water monitoring system 20. The water quality predicting system 10, in this manner, may request and receive water quality measures from the station-A (or any other monitoring station) for a specific time-span, such as past four months, past two days, or any other time-span.

The water quality predicting system 10, for example, may request the water quality measures in response to a request from the user device 50. Alternatively or in addition, the water quality predicting system 10 may request the water quality measures according to a predetermined schedule, such as hourly, daily, weekly, monthly, or any other predetermined schedule. The water quality predicting system 10 uses the water quality measures from the water monitoring system 20 to predict water quality of the water from the water source 30. The water quality predicting system 10 may predict the water quality over a forecast horizon, which may include multiple time-periods, such as days, weeks, months, or any other time-periods. Additionally, the water quality predicting system 10 predicts the water quality at a specific location, or locations. Thus, the water quality predicting system 10 predicts the water quality over time and space. For example, the water quality predicting system 10 predicts the water quality at station-B 24 and station-N 26 for six months July-December based on water quality measures from January-June.

In addition to the water quality measures from the water monitoring system 20, the water quality predicting system 10 may use data from the external data sources 40. The external sources 40 may include such disparate sources such as satellite images 42, expert reports 44, social media feeds 46, and other such data sources and a combination thereof.

The external data sources 40 may include remote data repositories, such as server computers, or any other data repositories that provide data either upon request, or according to a predetermined schedule. Of course, the external data sources 40 may include various other sources and types of data sources other than those illustrated in FIG. 1. For example, the external data sources may include weather data, anomalies at the water sources, such as a failure of a pumping station, or any other such data.

The satellite images 42 include satellite imagery of the water source 30. The satellite imagery may include images collected over duration, such as past five years, past six months, past two months, and so on. The water quality predicting system 10 may access the expert reports 44 from predetermined sources, such as remote servers hosted by environmental agencies, news organizations, and other data providers. The water quality predicting system 10 analyzes the satellite images 42 to identify changes in the water source 30. For example, if a satellite image is available for the station-A 22 that shows algae, the water quality predicting system 10 identifies and records the observation that algae level is high at the station-A 22 for the corresponding time period when the satellite image was taken. The water quality predicting system 10, in an example may request the remote servers that host the satellite images 42 for the satellite image at the station-A 22 at a specific time. Alternatively or in addition, the water quality predicting system 10 identifies that the satellite image corresponds to the station-A 22 and that the image is captured at the specific time based on a timestamp and geolocation associated with the satellite image.

Alternatively or in addition, the water quality predicting system 10 may analyze a sequence of satellite images captured along the flow of the water source 30 or temporal series of satellite images captured at the station-A 22. The water quality predicting system 10 may use image processing to transform the sequence of the satellite images into a time series corresponding to a water quality measure of the water source 30. For example, based on a series of the satellite images 42 along the flow of the water source 30, the water quality predicting system 10 may identify an increase in turbidity (or decrease in water clarity), and incorporates the observed trend into a model used for predicting the water quality.

The expert reports 44 include reports from experts about the water source 30 and surroundings. The water quality predicting system 10 may access the expert reports 44 from predetermined sources, such as remote servers hosted by environmental agencies, news organizations, and other data providers. The water quality predicting system 10 may analyze the expert reports 44 using syntactic and semantic analysis of the contents of the expert reports 44. The water quality predicting system 10, based on the expert reports 44, may identify a cause-effect relationship between an observation and a change in the water quality. For example, the expert reports 44 may indicate that water temperature, water flow, and aquatic plants directly affect the amount of dissolved oxygen in the water. The water quality predicting system 10 may constrain the model used for predicting the water quality based on the expert reports 44. Accordingly, the water quality predicting system 10 may use the water quality measures for the water source 30 to predict the water quality of the water source, based on the analysis in the expert reports.

The water quality predicting system 10, additionally or alternatively, may access the social media 46 to identify causal events that may be used by the model for predicting the water quality. For example, the social media 46 may include social network posts associated with the water source 30. The social network posts may include text, image, audio, video, or any other content. For example, the social network post may include a post to FACEBOOK®, TWITTER®, INSTAGRAM®, PINTEREST®, GOOGLE+®, or any other social network. The social network post may additionally include content posted on a news website, blog, or any other website. For example, the water quality predicting system 10 may access an image or a text in the social network post and convert the same into an observation. For example, the water quality predicting system 10 may analyze the image to identify that the algae level is high, based on image processing of the image, or textual analysis of text in the social network post. The water quality predicting system 10 may identify the social network post being associated with the water source 30 using geolocation associated with the social network post. The water quality predicting system 10 may access social media 46 to obtain the social network posts from a specific time period and those that have a geolocation of the water source 30. Alternatively or in addition, the data repositories that store the social media 46 may transmit the social network posts that are associated with the geolocation of the water source 30 to the water quality predicting system 10. In an example, the water quality predicting system 10 may use the observations obtained by converting the social media 46 to confirm the observations from other data sources, such as the satellite images 42.

The water quality predicting system 10 may output the predicted water quality measures. For example, the water quality predicting system 10 may transmit the predicted water quality measures to the user device 50. Alternatively, the water quality predicting system 10 compares the predicted water quality measures with predetermined thresholds that are indicative of safety levels. For example, a safety level may indicate a level of contamination above which the water may be considered unsafe for consumption, such as for drinking, cooking, using for particular industrial processes, or any other type of consumption. For example, the safety level may indicate a threshold for a safe amount of contaminants like lead, mercury, oxygen, chlorophyll, chlorine, algae, or any other contaminant or a combination thereof. If the predicted water quality measures indicate that the safety thresholds are being exceeded, and thus the water is unsafe, the water quality predicting system 10 may send an alert for reception by the user device 50.

The user device 50 may be communication apparatus, such as a laptop computer, a desktop computer, a tablet computer, a server computer, a phone, a smartphone, a wearable device, or any other apparatus that can receive communication messages. For example, the user device 50 may be a device by which a water management body of the water source 30 receives communication messages. For example, the water management body may be a local governing body, a private organization, or any other organization that manages the quality of the water source 30. Alternatively or in addition, the user device 50 may be communication apparatus of a user that consumes the water from the water source 30. For example, the user may be an individual, a restaurant, a factory, a shop, a business, or any other entity that gets water from the water source.

Figure 1B:
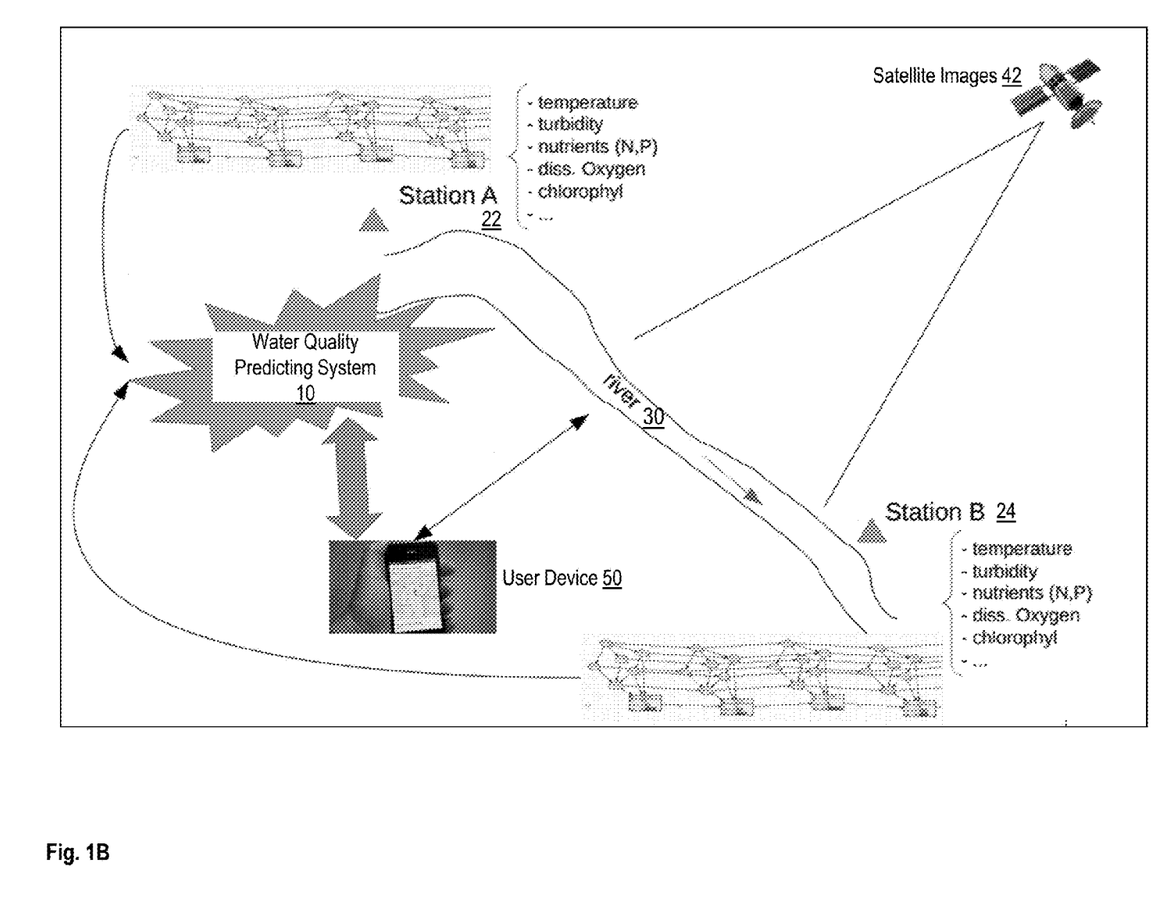
FIG. 1B illustrates an example use of the water quality predicting system in accordance with an embodiment.

FIG. 1B illustrates an example use of the water quality predicting system in accordance with an embodiment, where the water source 30 is a river basin.

Figure 2:
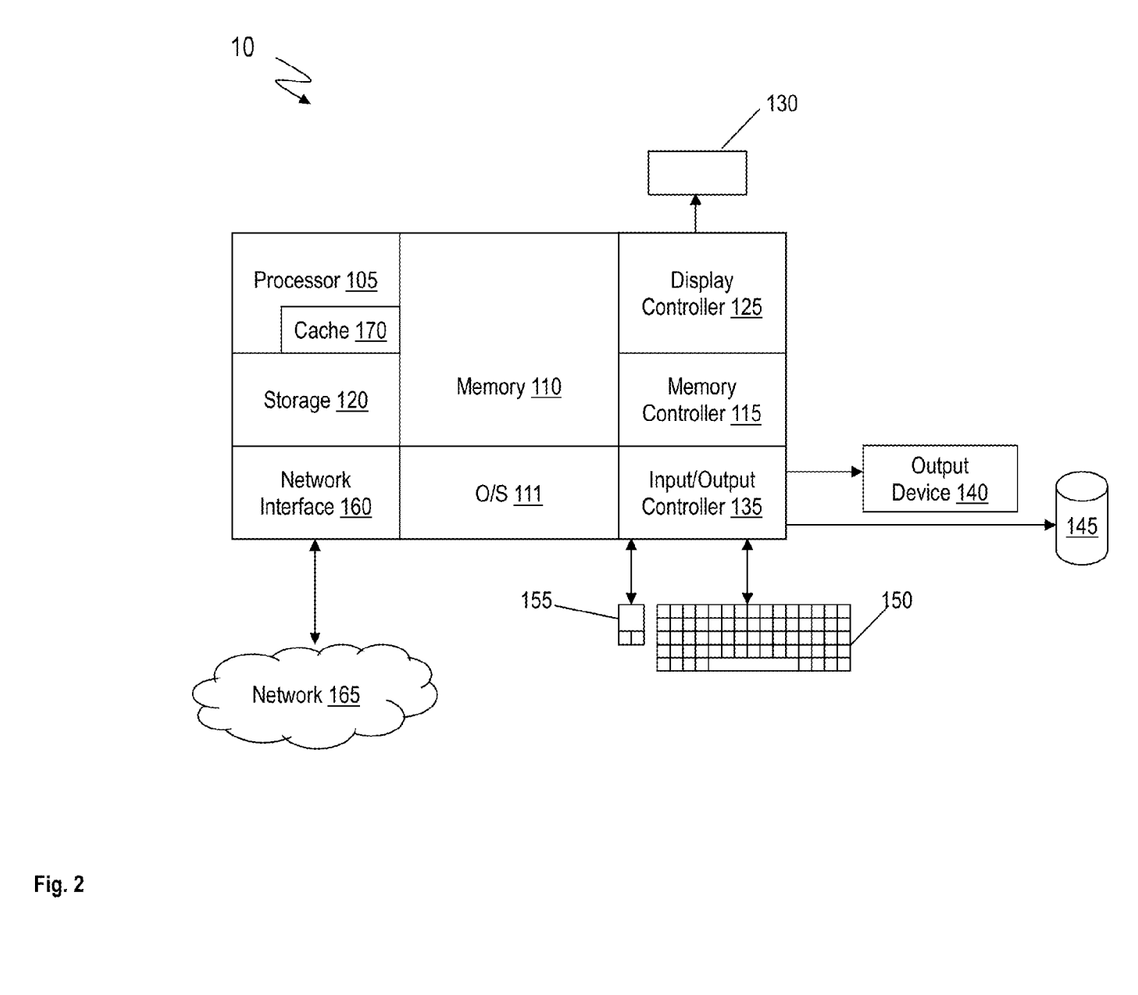
FIG. 2 illustrates a view of example components of a water quality predicting system in accordance with an embodiment.

FIG. 2 illustrates a view of example components of the water quality predicting system 10. The water quality predicting system 10 may be a communication apparatus, such as a computer. For example, the water quality predicting system 10 may be a desktop computer, a tablet computer, a laptop computer, a phone, such as a smartphone, a server computer, or any other device that communicates via the network 165. The water quality predicting system 10 includes hardware, such as electronic circuitry.

The water quality predicting system 10 includes, among other components, a processor 105, memory 110 coupled to a memory controller 115, and one or more input devices 145 and/or output devices 140, such as peripheral or control devices, that are communicatively coupled via a local I/O controller 135. These devices 140 and 145 may include, for example, battery sensors, position sensors (altimeter, accelerometer, GPS), indicator/identification lights and the like. Input devices such as a conventional keyboard 150 and mouse 155 may be coupled to the I/O controller 135. The I/O controller 135 may be, for example, one or more buses or other wired or wireless connections, as are known in the art. The I/O controller 135 may have additional elements, which are omitted for simplicity, such as controllers, buffers (caches), drivers, repeaters, and receivers, to enable communications.

The I/O devices 140, 145 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 105 is a hardware device for executing hardware instructions or software, particularly those stored in memory 110. The processor 105 may be a custom made or commercially available processor, a central processing unit (CPU), an auxiliary processor among several processors associated with the water quality predicting system 10, a semiconductor based microprocessor (in the form of a microchip or chip set), a macroprocessor, or other device for executing instructions. The processor 105 includes a cache 170, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 170 may be organized as a hierarchy of more cache levels (L1, L2, and so on.).

The memory 110 may include one or combinations of volatile memory elements (for example, random access memory, RAM, such as DRAM, SRAM, SDRAM) and nonvolatile memory elements (for example, ROM, erasable programmable read only memory (EPROM), electronically erasable programmable read only memory (EEPROM), programmable read only memory (PROM), tape, compact disc read only memory (CD-ROM), disk, diskette, cartridge, cassette or the like). Moreover, the memory 110 may incorporate electronic, magnetic, optical, or other types of storage media. Note that the memory 110 may have a distributed architecture, where various components are situated remote from one another but may be accessed by the processor 105.

The instructions in memory 110 may include one or more separate programs, each of which comprises an ordered listing of executable instructions for implementing logical functions. In the example of FIG. 2, the instructions in the memory 110 include a suitable operating system (OS) 111. The operating system 111 essentially may control the execution of other computer programs and provides scheduling, input-output control, file and data management, memory management, and communication control and related services.

Additional data, including, for example, instructions for the processor 105 or other retrievable information, may be stored in storage 120, which may be a storage device such as a hard disk drive or solid state drive. The stored instructions in memory 110 or in storage 120 may include those enabling the processor to execute one or more aspects of the systems and methods of this disclosure.

The water quality predicting system 10 may further include a display controller 125 coupled to a user interface or display 130. In some embodiments, the display 130 may be an LCD screen. In other embodiments, the display 130 may include a plurality of LED status lights. In some embodiments, the water quality predicting system 10 may further include a network interface 160 for coupling to a network 165. The network 165 may be an IP-based network for communication between the water quality predicting system 10 and an external server, client and the like via a broadband connection. In an embodiment, the network 165 may be a satellite network. The network 165 transmits and receives data between the water quality predicting system 10 and external systems. In some embodiments, the network 165 may be a managed IP network administered by a service provider. The network 165 may be implemented in a wireless fashion, for example, using wireless protocols and technologies, such as Wi-Fi, WiMAX, satellite, or any other. The network 165 may also be a packet-switched network such as a local area network, wide area network, metropolitan area network, the Internet, or other similar type of network environment. The network 165 may be a fixed wireless network, a wireless local area network (LAN), a wireless wide area network (WAN) a personal area network (PAN), a virtual private network (VPN), intranet or other suitable network system and may include equipment for receiving and transmitting signals.

Figure 3:
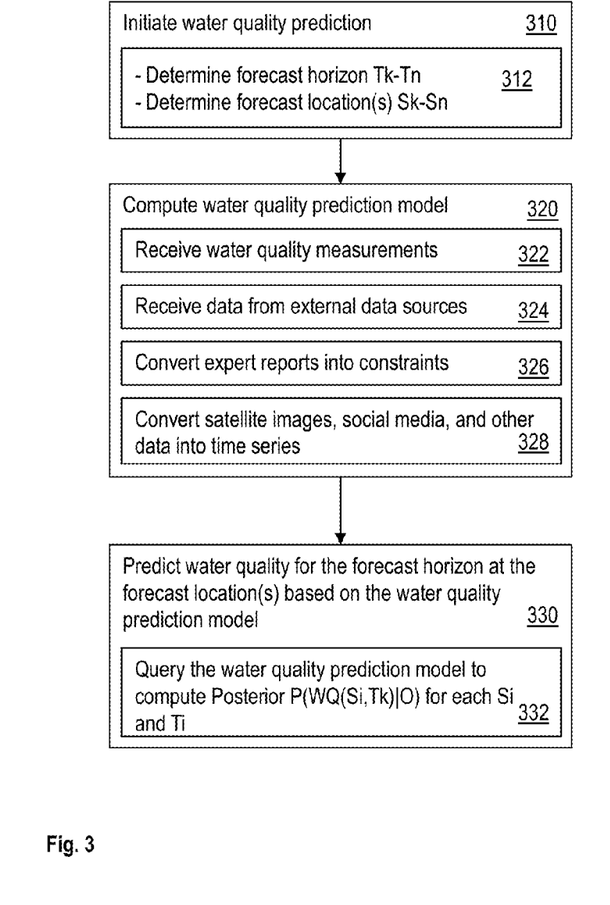
FIG. 3 illustrates a flowchart of an example method for predicting water quality in accordance with an embodiment.

FIG. 3 illustrates a flowchart of an example method for predicting water quality. The water quality predicting system 10 may implement the example method, for example using the one or more components described herein. The water quality predicting system 10 initiates the water quality prediction, as shown at block 310. For example, the initiation may be in response to a request received from the user device 50. Alternatively or in addition, the initiation may be in response to a predetermined water quality prediction schedule, such as an hourly/daily/weekly/monthly or any other periodic water quality prediction schedule. The water quality predicting system 10 determines a forecast horizon and a forecast location(s) for which to predict the water quality, as shown at block 312. In case the water quality prediction is in response to the request from the user device 50, the water quality predicting system 10 receives the forecast horizon and the forecast locations as part of the request.

The forecast horizon is a set of time periods for which to predict the water quality. For example, the forecast horizon may include T1 . . . Tn time periods, where each time period may be a month, a week, a fortnight, or any other time period. The forecast locations may include a set of geographic locations associated with the water source 30 at which to predict the water quality. For example, the forecast locations may be the monitoring stations of the water monitoring system 20. Consider that the set of forecast locations is S with locations S1 . . . Sm, in that order along the flow of the water source 30, that is Si+1 is downstream from Si, and is successively adjacent to Si, unless stated otherwise.

The water quality predicting system 10 computes a water quality prediction model, as shown at block 320. The water quality predicting system 10 may compute a model for each station Si in the set of forecast locations S. To compute the water quality prediction model, the water quality predicting system 10 receives water quality measurements from the water monitoring system 20, as shown at block 322. The water monitoring system 20 may transmit the water quality measurements in response to a request from the water quality predicting system 10. The water quality predicting system 10 may also receive data from the external data sources 40, as shown at block 324. The water quality predicting system 10 may receive the data from the external data source 40 in response to requesting the data. The water quality predicting system 10 analyzes and process the data received. For example, the water quality predicting system 10 converts the data from the expert reports 44 into constraints for the water quality prediction model, as shown at block 326. The water quality predicting system 10 may convert other data from the external data sources into evidence, for example, the satellite images 42 and social media 46, into time series data, as shown at block 328.

Figure 4:
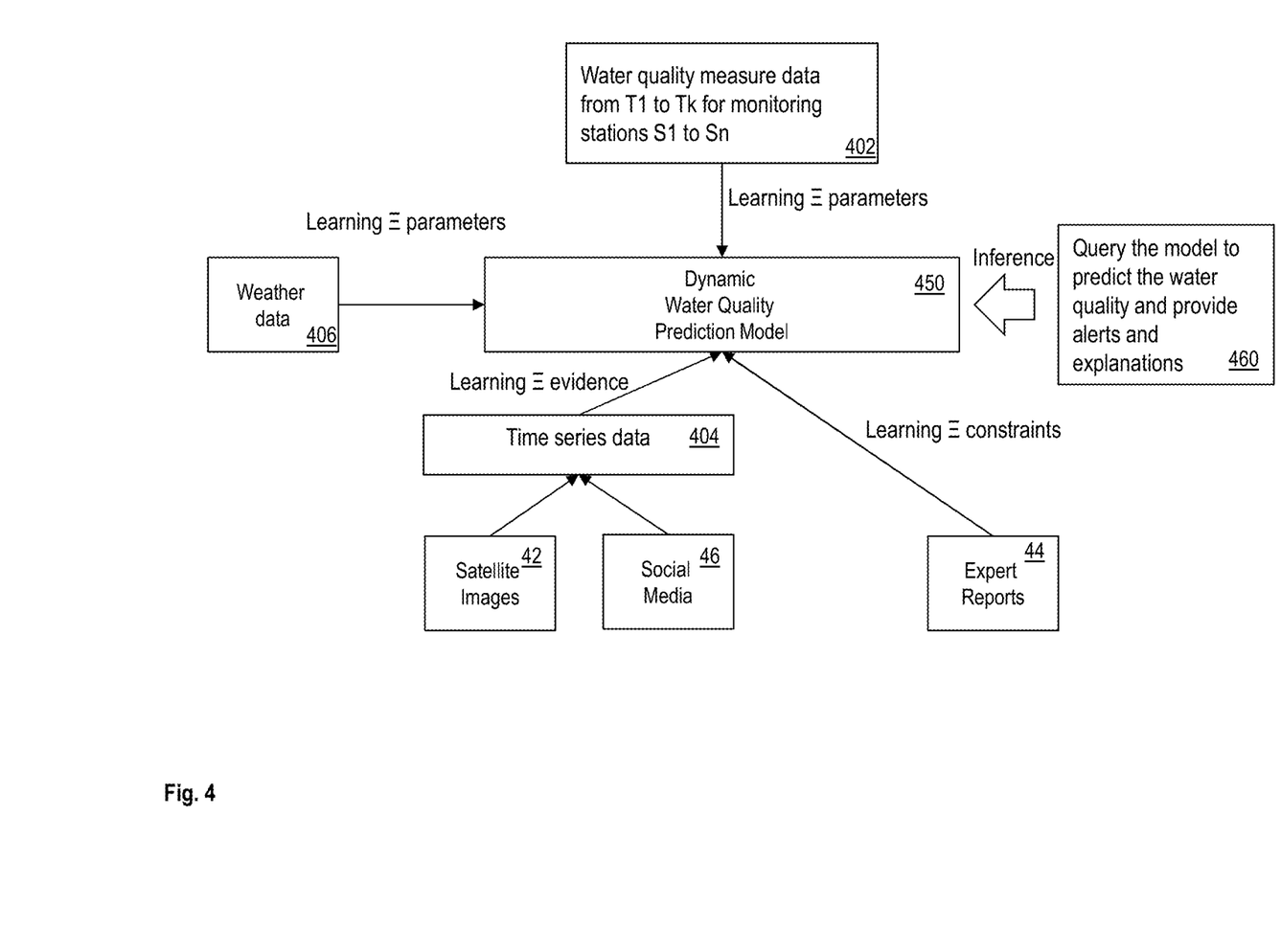
FIG. 4 illustrates an example computation of a dynamic water quality prediction model in accordance with an embodiment.

FIG. 4 illustrates an example computation of a dynamic water quality prediction model 450 using Bayesian networks. A Bayesian network models observed variables and their relationships. The water quality prediction model 450 facilitates computing the predicted water quality measures by computing posterior distribution of variables given evidence variables, which may be referred to as probabilistic inference. Further, by using a water quality prediction model 450 that is based on Bayesian network, the water quality predicting system provides explanations of hazardous situations caused due to water quality being below predetermined safety levels. Further yet, the water quality predicting system 10 uses a dynamic Bayesian network to compute the model 450, which relates variables to each other over adjacent time periods.

The computation uses, as input variables, periodic water quality measurements 402. The water quality measurements are from the monitoring stations S1-Sm of the water monitoring system 20, and are for the time periods T1-Tk, where Tk is the current time period, and the forecast horizon is Tk+1 to Tn. The computation further uses satellite images 42 of the water source 30. The computation additionally uses user images, news, tweets, and other social media 46 about events along the water source 30. The water quality predicting system 10 converts by the system into observations. For example, as described earlier, the water quality predicting system 10 converts the data into time series data 404 by performing image analysis and/or text analysis of the data. The observations obtained from the time series data 404 may be used as evidence in the Bayesian network. The computation may further use weather data 406, which may include periodic weather measurements, such as temperature, precipitation, and the like from a set of weather stations. Thus, based on the current observations, the water quality measurement 402 for the first k time periods, the weather measurements 406, and the time series data 404, the water predicting system 10 computes the dynamic water quality prediction model for the forecast horizon H=Tk+1 . . . Tn time periods and locations (S1, . . . , Sm).

The water quality predicting system 10 may use the water quality measure data 402 and the weather data 406 to identify the parameters that affect the water quality. For example, the water quality predicting system 10 may use Bayesian networks to identify the parameters. For example, the water quality predicting system 10 may use an algorithm such as expectation maximization (EM) algorithm for finding maximum likelihood or maximum a posteriori (MAP) estimates of potential parameters in the water quality prediction model 450. For example, the water quality predicting system 10 iteratively alternates between performing an expectation (E) step, which creates a function for the water quality based on parameter measurements from time periods T1 to Tk-1, and evaluates the findings using the current parameters for time period Tk. The water quality predicting system further performs a maximization (M) step, which computes parameters maximizing the results of the E step. The parameter-estimates are then used to determine the distribution of the latent variables in the next E step.

Thus, for each location Si in S, the water quality prediction system 10 computes the water quality prediction model M(Si). For learning the model M(Si), the water quality predicting system 10 uses the historical data recorded to learn the dynamic Bayesian network M(Si) with T time slices, where T is the number of time periods T1-Tn. For example, the water quality measures 402, the weather measurements 406 are the variables in the model 450. Additionally, the water quality predicting system 10 uses causal background/expert knowledge (if available) to enforce constraints in the model M(Si). For example, if the expert reports 44 indicate that water temperature, flow, or aquatic plants are known to affect the amount of dissolved oxygen in the water, the water quality predicting system 10 notes the mapping between the causal variable and the water quality measurement parameter.

Further, the water quality predicting system 10 marks the variables that define the water quality measure. For example, water quality may be reflected by a measure of the amount of dissolved oxygen in the water. In another example, the water quality may be based on a combination of variables, such as the dissolved oxygen and the turbidity. The combination of the variables may be assigned different weighting schemes.

The water quality predicting system 10 further combines the models computed for each of the stations S1-Sm. For example, for pairs of successive stations (Si, Si+1) such that Si+1 is downstream of Si, the water quality predicting system 10 combines M(Si) with M(Si+1) by adding conditional probabilities, such as P(WQ(Si+1)|WQ(Si)), where WQ(Si) are the water quality variables corresponding to location Si. Thus, the water quality predicting system 10 use the historical water quality measure data 402 to learn the parameters of the P(WQ(Si+1)|WQ(Si)) distributions.

Returning to FIG. 3, the water quality predicting system 10 predicts the water quality for the forecast horizon at the forecast location(s) based on the water quality prediction model 450, as shown at block 330. For example, and referring to FIG. 4, the water quality predicting system 10 queries the model 450 to compute the water quality predictions, as shown at block 460.

For example, the water quality predicting system 10 queries the water quality prediction model 450 to compute posterior P(WQ(Si, Tk)|O) for each Si and Ti, as shown at block 332 of FIG. 3. Here, O is the current set of observations (values of variables) up to current time period Tk, where T1<=Tk<Tn. The observations may be for measurements such as temperatures, water flows, oxygen levels, or any other measurement values from the monitoring stations or the weather stations. In addition, the observations may include the parameters from conversion and analysis of the external data sources 40.

Based on the observation data, the water quality predicting system 10 predicts the water quality for each of the subsequent time periods Tk+1, Tk+2, . . . , up to Tn. The water quality predicting system 10 computes posterior distribution P(WQ|O), at each location Si. For example, the posterior distribution of the dissolved oxygen levels at each of the locations for the next p time periods or to the end of T. Thus, the water quality predicting system 10 computes posterior probability distribution of water quality for each of the (n-k) future time periods and locations. The water quality predicting system 10 may output the computed water quality predicted values. In addition, the water quality predicting system 10 provides an explanation for each of the predicted values. For example, the water quality predicting system 10 may predict that—"possible low dissolved oxygen levels in August due to algae bloom in May".

Figure 5:
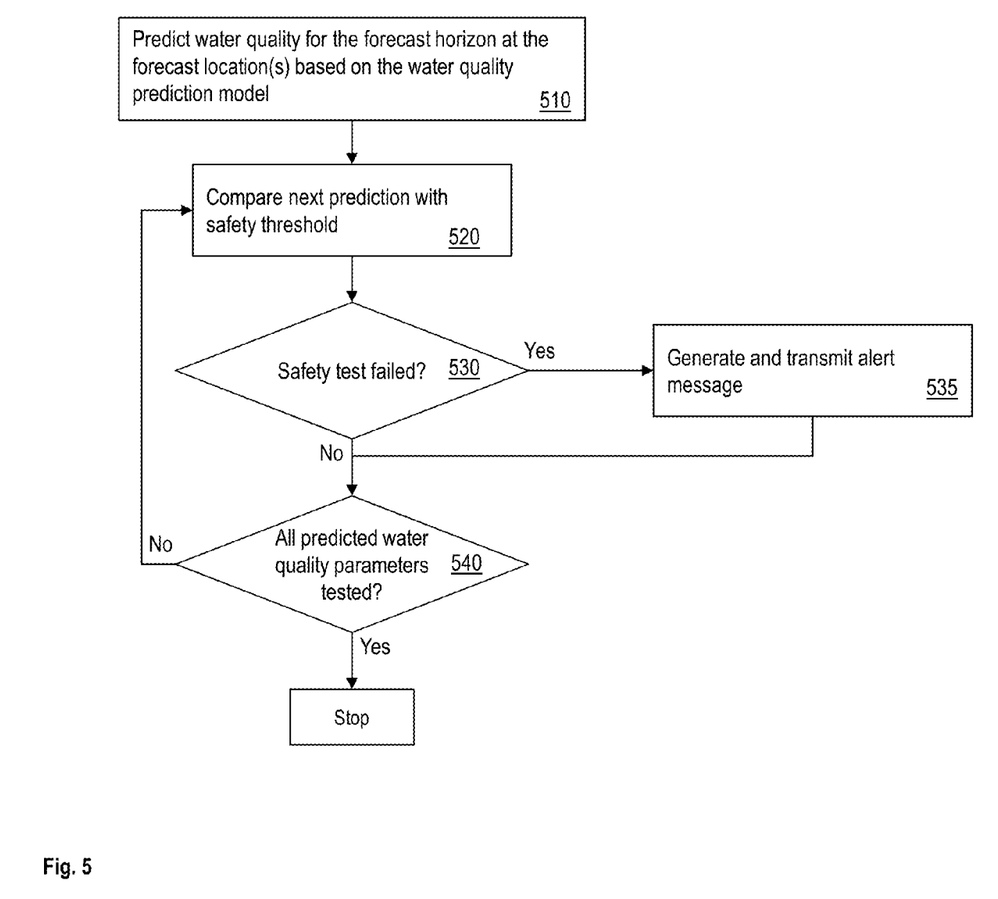
FIG. 5 illustrates a flowchart of an example method for transmitting an alert message in accordance with an embodiment.

FIG. 5 illustrates a flowchart of an example method in which the water quality predicting system 10 transmits an alert message based on the predicted water quality. For example, the water quality predicting system 10 predicts the water quality for the forecast horizon at the forecast location (s) based on the water quality prediction model 450, as shown at block 510. Upon computing the predicted water quality measurements, the water quality predicting system 10 compares the predicted water quality measurements with predetermined safety thresholds, as shown at block 520. In case the safety test fails, that is the safety threshold is exceeded (or not exceeded), the water quality predicting system 10 generates an alert message, as shown at blocks 530 and 535. For example, the water quality predicting system 10 generates an alert message if P(WQ|O) exceeds a predefined thresholds. For example, if P(WQ=low O)>0.7, which indicates that there is a 70% chance that the levels of oxygen are going to be low over the next 3 months. The water quality predicting system, in response to generating the alert message, generates an explanation for the possible water quality event causing the alert message for the specific location along the water source. For example, based on the water quality prediction mode, the water quality predicting system may determine the explanation and transmit the explanation as part of, or in conjunction with the alert message. For example, the explanation may identify that low dissolved oxygen levels in August downstream of Bellevue, Iowa were caused due to high levels of chlorophyll in June-July caused by an algae bloom. The water quality predicting system 10 ensures that each of the predicted water quality parameter is tested, as shown at block 540.

Thus, the technical solutions described herein facilitate predicting water quality over a set of time periods and alert users if probability of water quality exceeds (or is below) a predetermined threshold. Additionally, the technical solutions generate an explanation (in natural language) for water quality events. The technical solutions use machine-learning techniques, such as Bayesian network, to predict the water quality over time and space. Thus, the technical solutions provide a temporal/dynamic as well as spatial model that integrates multiple data sources, predicts/monitors water quality at multiple locations, and exploits spatial dependencies between adjacent locations. Since the water prediction model is dynamic in nature, as opposed to a static model (that is computed once and used over and over), the technical solutions described herein improve the accuracy of the water quality prediction as the prediction relies on more current information which may be obtained from disparate sources as described herein.

The present technical solutions may be a system, a method, and/or a computer program product at any possible technical detail level of integration. The computer program product may include a computer readable storage medium (or media) having computer readable program instructions thereon for causing a processor to carry out aspects of the present technical solutions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technical solutions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present technical solutions.

Aspects of the present technical solutions are described herein with reference to flowchart illustrations and/or block diagrams of methods, apparatus (systems), and computer program products according to embodiments of the technical solutions. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present technical solutions. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are to be construed in the broadest sense, superseding any other implied definitions hereinbefore or hereinafter unless expressly asserted to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

The descriptions of the various embodiments of the present technical solutions have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application, or technical improvement over technologies found in the marketplace, or to enable others of ordinary skill in the art to understand the embodiments disclosed herein.

What is claimed is:

1. A computer implemented method for predicting water quality of a water source, the method comprising:
   receiving, from a user device, a forecast horizon for across which to predict the water quality, wherein the forecast horizon comprises a plurality of time periods ($T_1$-$T_n$);
   receiving, from the user device, one or more geographical locations ($S_1$-$S_p$) at which to predict the water quality;
   receiving, from a monitoring stations at each of the one or more geographical locations, a set of present water quality measures for the water source;
   receiving, from an external source, an expert report about the water source and surroundings;
   receiving satellite imagery of the one or more geographical locations ($S_1$-$S_p$);
   in response to detecting changes in the water quality based on the satellite imagery, requesting, from remote servers hosting the satellite images, satellite imagery of the one or more geographical locations ($S_1$-$S_p$) at which a change in water quality occurred for specific time periods;
   generating, by a water quality prediction system, a water quality prediction model $M(S_i)$ for each geographical location $S_i$ from the one or more geographical locations using historical water quality data at the each geographical location $S_i$ and the satellite imagery for the specific time periods, the model $M(S_i)$ mapping a causal variable with each water quality measure from the set of water quality measures, wherein the combined water quality prediction models are constrained by an analysis in the expert report;
   combining, by the water quality prediction system, the water quality prediction model for a geographical location $S_{i+1}$ with the water prediction model for $S_i$ by adding a conditional probability;
   determining, by the water quality prediction system, predicted water quality measures for each of the geographical locations $S_i$ at each time period $T_k$ from the plurality of time periods in the forecast horizon based on the combined water quality prediction models for each geographical locations $S_i$ using the present water quality measures, wherein a first predicted water quality measure for the geographical location $S_i$ at a time period $T_k$ is based on a second predicted water quality measure for the geographical location $S_i$ at time periods $T_1$ to $T_{k-1}$;
   in response to a predicted water quality measure being below a predetermined threshold, generating, by the water quality prediction system, an explanation in natural language based on the causal variable mapped with the water quality measure that is predicted; and
   outputting, by the water quality prediction system, for receipt by the user device, the predicted water quality measure and the explanation.

2. The computer implemented method of claim 1, wherein the set of present water quality measures is received from a geographical location $S_{p+1}$ that is upstream from the geographical locations at which the water quality is predicted.

3. The computer implemented method of claim 1, wherein the water quality measure comprises dissolved oxygen, turbidity, and a combination thereof.

4. The computer implemented method of claim 1, wherein the predicted water quality measures are determined based on a Bayesian network.

5. The computer implemented method of claim 1, further comprising:
   transmitting, by the water quality prediction system, for receipt by the user device, an alert in response to the predicted water quality measure being indicative of contamination above a predetermined threshold.

6. The computer implemented method of claim 5, further comprising:
   transmitting, by the water quality prediction system, for receipt by the user device, an explanation of the predicted water quality measure being indicative of the contamination above the predetermined threshold.

7. A system for predicting water quality of a water source, the system comprising:
   a memory; and
   a processor configured to:
      receive, from a user device, a forecast horizon for across which to predict the water quality, wherein the forecast horizon comprises a plurality of time periods ($T_1$-$T_n$);
      receive, from the user device, a one or more geographical locations ($S_1$-$S_k$) at which to predict the water quality;
      receive, from a monitoring stations at each of the one or more geographical locations, a set of water quality measures for the water source;
      receive, from an external source, an expert report about the water source and surroundings;
      receive satellite imagery of the one or more geographical locations ($S_1$-$S_p$);
      in response to detecting changes in the water quality based on the satellite imagery, request, from remote servers hosting the satellite images, satellite imagery of the one or more geographical locations ($S_1$-$S_p$) at which a change in water quality occurred for specific time periods;

generate a water quality prediction model $M(S_i)$ for each geographical location $S_i$ from the one or more geographical locations using historical water quality data at the each geographical location $S_i$ and the satellite imagery for the specific time periods, the model $M(S_i)$ mapping a causal variable with each water quality measure from the set of water quality measures;

combine the water quality prediction model for a geographical location $S_{i+1}$ with the water prediction model for $S_i$ by adding a conditional probability;

determine predicted water quality measures each of for the geographical locations $S_i$ at each time period $T_k$ from the plurality of time periods in the forecast horizon based on the combined water quality prediction models for each geographical locations $S_i$ using the water quality measures, wherein a first predicted water quality measure for the geographical location $S_i$ at a time period $T_k$ is based on a second predicted water quality measure for the geographical location $S_i$ at time periods $T_1$ to $T_{k-1}$, wherein the combined water quality prediction models are constrained by an analysis in the expert report;

in response to a predicted water quality measure being below a predetermined threshold, generate an explanation in natural language based on the causal variable mapped with the water quality measure that is predicted; and output, for receipt by the user device, one or more of the predicted water quality measures and the explanation.

8. The system of claim 7, wherein the set of water quality measures is received from a geographical location $S_{p+1}$ that is upstream from the geographical locations at which the water quality is predicted.

9. The system of claim 7, wherein the water quality measure comprises dissolved oxygen, turbidity, and a combination thereof.

10. The system of claim 7, wherein the predicted water quality measures are determined based on images of the water source uploaded on a social media data repository.

11. The system of claim 7, wherein the processor is further configured to:

transmit, for receipt by the user device, an alert in response to a predicted water quality measure being indicative of contamination above a predetermined threshold.

12. The system of claim 11, wherein the processor is further configured to:

transmit, for receipt by the user device, an explanation of the predicted water quality measure being indicative of the contamination above the predetermined threshold.

13. A computer program product for predicting water quality of a water source, the computer program product comprising a computer readable storage medium, the computer readable storage medium comprising computer executable instructions, wherein the computer readable storage medium comprises instructions to:

receive, from a user device, a forecast horizon for across which to predict the water quality, wherein the forecast horizon comprises a plurality of time periods ($T_1$-$T_n$);

receive, from the user device, a one or more geographical locations ($S_1$-$S_k$) at which to predict the water quality;

receive, from a monitoring stations at each of the one or more geographical locations, a set of water quality measures for the water source;

receive, from an external source, an expert report about the water source and surroundings;

receive satellite imagery of the one or more geographical locations ($S_1$-$S_p$);

in response to detecting changes in the water quality based on the satellite imagery, request, from remote servers hosting the satellite images, satellite imagery of the one or more geographical locations ($S_1$-$S_p$) at which a change in water quality occurred for specific time periods;

generate a water quality prediction model $M(S_i)$ for each geographical location $S_i$ from the one or more geographical locations using historical water quality data at the each geographical location $S_i$ and the satellite imagery for the specific time periods, the model $M(S_i)$ mapping a causal variable with each water quality measure from the set of water quality measures;

combine the water quality prediction model for a geographical location $S_{i+1}$ with the water prediction model for $S_i$ by adding a conditional probability;

determine predicted water quality measures each of for the geographical locations $S_i$ at each time period $T_k$ from the plurality of time periods in the forecast horizon based on the combined water quality prediction models for each geographical locations $S_i$ using the water quality measures, wherein a first predicted water quality measure for the geographical location $S_i$ at a time period $T_k$ is based on a second predicted water quality measure for the geographical location $S_i$ at time periods $T_1$ to $T_{k-1}$, wherein the combined water quality prediction models are constrained by an analysis in the expert report;

in response to a predicted water quality measure being below a predetermined threshold, generate an explanation in natural language based on the causal variable mapped with the water quality measure that is predicted; and output, for receipt by the user device, one or more of the predicted water quality measures and the explanation.

14. The computer program product of claim 13, wherein the predicted water quality measures are determined based on images of the water source uploaded on a social media data repository.

15. The computer program product of claim 13, wherein the computer readable storage medium comprises instructions to:

transmit, for receipt by the user device, an alert in response to a predicted water quality measure being indicative of contamination above a predetermined threshold.

16. The computer program product of claim 15, wherein the transmission further comprises an explanation of the predicted water quality measure being indicative of the contamination above the predetermined threshold.

17. The computer program product of claim 13, wherein the water quality measure comprises dissolved oxygen, turbidity, and a combination thereof.

* * * * *